US006452680B1

(12) United States Patent
Paldus et al.

(10) Patent No.: US 6,452,680 B1
(45) Date of Patent: Sep. 17, 2002

(54) CAVITY RING DOWN ARRANGEMENT FOR NON-CAVITY FILLING SAMPLES

(75) Inventors: Barbara A. Paldus, Sunnyvale, CA (US); Charles Harb, Palo Alto, CA (US); Richard N. Zare, Stanford, CA (US); Gerard Meijer, Molenhoek (NL)

(73) Assignee: Informed Diagnostics, Inc., Sunnyvale, CA (US)

( * ) Notice: Subject to any disclaimer, the term of this patent is extended or adjusted under 35 U.S.C. 154(b) by 0 days.

(21) Appl. No.: 09/497,309

(22) Filed: Feb. 3, 2000

(51) Int. Cl.[7] ............................................... G01N 21/00

(52) U.S. Cl. ........................ 356/436; 356/440; 250/343

(58) Field of Search .......................... 250/343; 356/439, 356/436, 437, 438, 440, 441, 442, 451, 454, 519

(56) References Cited

U.S. PATENT DOCUMENTS 5,912,740 A * 6/1999 Zare et al. .................. 356/437

* cited by examiner

Primary Examiner—Samuel A. Turner
Assistant Examiner—Patrick Connolly
(74) Attorney, Agent, or Firm—John F. Schipper

(57) ABSTRACT

Method and system for cavity ring down spectroscopic analysis of non-cavity-filling sample. An interface of a sample (gas, liquid, thin film, bulk solid, etc.) is positioned at a Brewster angle relative to a p-wave polarized light beam propagating in an optical cavity so that substantially no light beam energy is lost by reflection at the interface. The light beam cycles one or more times in the cavity for each of a sequence of selected wavelengths, is extracted from the cavity, and is analyzed to determine an absorption spectrum for the sample. The cavity, except for the sample region may be filled with a solid, optionally dielectrically active and optionally having an electrical field applied thereto to vary the solid's refractive index according to the light beam wavelength used.

38 Claims, 8 Drawing Sheets

CAVITY RING DOWN ARRANGEMENT FOR NON-CAVITY FILLING SAMPLES

FIELD OF THE INVENTION

This invention relates to spectroscopic analysis of chemical samples for the presence of, or characteristics of, one or more specified molecules.

BACKGROUND OF THE INVENTION

Cavity ring down spectroscopy (CRDS) is a laser-based, high sensitivity, absorption measurement technique that has become competitive with alternative techniques, such as intra-cavity laser absorption spectroscopy, frequency modulation spectroscopy, multipass spectroscopy and photoacoustic spectroscopy, for performing spectroscopic analysis of a sample. CRDS exploits the properties of a high finesse optical resonator, usually formed by two or more high reflectivity mirrors defining an optical cavity, with a sample located in the optical cavity. A narrow bandwidth laser light beam is injected into the optical resonator and abruptly terminated. The resulting rate of decay, R, of light beam intensity is measured and is linearly related to the optical resonator losses by a relation $$R = 1/\tau = L_{tot}/\Delta t_{rt}, \quad (1)$$

$$L_{tot} = L(\text{refl}) + L(\text{sample}). \quad (2)$$

Here $\tau$ is the ring down decay constant (sec), $\Delta t_{rt}$ is the optical cavity round trip time, and $L(\text{refl})$ and $L(\text{sample})$ are measures of the light beam intensity losses due to the resonator alone (no sample present) and due to sample absorption and scattering, respectively, at the chosen wavelength.

In the past, CRDS has been primarily applied to gas phase samples, because of the relative simplicity of such samples. For a typical gas sample, an absorption spectral scan of cavity losses with no sample present is first performed to serve as a reference. Subsequently, the sample gas is injected into and substantially fills the cavity, and total sample absorption spectrum is again measured. The final quantitative measurement of the gas absorption is determined by subtracting the reference spectrum from the total spectrum. Because a gas fills the optical cavity uniformly, the light beam circulating within the cavity will be substantially uniformly absorbed along the entire round trip route along the resonator. Thus, no corrections need be made for the shape of the light beam within the optical cavity or for the unknown length of the sample, in order to obtain a fully quantitative measurement. In certain instances, the optical resonator, also referred to as a ring down cavity (RDC), encloses a sample having a finite length that is shorter than the length of the RDC. In particular, a flame having a known geometry has been studied for its composition, temperature and species profile(s) using CRDS.

Unless the sample gas contains particulates, such as dust, the gas will produce negligible scattering of the light beam within the RDC. Further, a gas that fills the cavity has no reflecting facets produced by a physical interface between the sample and the remainder (if any) of the volume within the RDC that can interfere with the light beam.

For a condensed phase sample, such as a liquid, thin film or bulk solid, or a gas that does not fill the cavity, however, these problems are present and would appear to preclude use of CRDS as an absorption measurement tool. If a condensed phase or gas sample is positioned at random within, but does not fill, a high finesse optical resonator that includes two or more mirrors and contains a gas or a vacuum, one or more physical interfaces between the sample and the remainder of the RDC volume is created. The interface(s) can produce reflection losses inside the RDC that far exceed the other losses associated with the RDC and would compromise the observation of a single exponential decay of light beam intensity at the RDC output terminal, by formation of coupled resonators. Because light beam intensity losses per unit length within a condensed phase sample tend to be large, filling the RDC with this sample would severely degrade the resonator finesse and thus interfere with a straightforward measurement of the ring-down signal and reduce sensitivity to different samples. If the round trip length of the resonator is reduced in order to minimize the sample length, the decay constant for, and sensitivity to, the sample within the RDC would be correspondingly reduced.

For a non-cavity-filling sample, the sample length within the RDC must be chosen so that the total sample losses are comparable to the RDC optical losses, and so that the ring-down decay constant does not become too small for accurate detection by the available electronics. One approach to this problem is to probe the sample within the RDC with an evanescent wave that is external to the RDC, as proposed by Pipino et al [U.S. Pat. No. 5,943,136]. In one embodiment of the Pipino et al approach, the RDC is a monolithic ring cavity, wherein the injected radiation is reflected by total internal reflection, thereby generating at each facet an evanescent wave whose path length within the sample is determined by the light beam wavelength, by the RDC refractive indices and by the nature of the sample. In an alternative embodiment, a Pelin-Broca prism is positioned within the RDC so that a light beam reflected at a prism facet produces a single evanescent wave that propagates within the sample. In both embodiments, the effective sample path length is determined by the light beam penetration depth, rather than by the sample round trip length within the RDC. The Pipino et al approach could have advantages in certain applications, but this approach can severely limit the sample length probed for a poorly absorbing sample, or for small concentrations of a sample that is sparsely distributed within a non-absorbing matrix. Typically, the effective sample penetration depth in evanescent wave CRDS is on the order of one-tenth of the radiation wavelength, or about 70 nm to 1 $\mu$m for radiation wavelength in the near infrared to mid-infrared region.

What is needed is a spectroscopic testing system that provides preparation and accurate testing for the presence of one or more target molecules that may be present in an amount ranging from an extremely small trace to a modest percentage of the sample contents, that can be used to test for the presence of one or more different molecules, that can provide confirmation or refutation of the postulated presence of one or more target molecules in as little as a few minutes, that can be quickly expanded to cover testing for other molecular markers, based on the initial test results, and that does not require performance of various wet chemistry procedures to determine whether a particular target molecule is present. Preferably, the system should have very small losses of the probe light beam. Preferably, the system should be small enough to located in the on-site office of test personnel, such as a medical doctor, a veterinarian, an industrial health and safety officer and the like. Preferably, the system should allow preservation of the sample(s) for further and possibly more elaborate testing at another time.

SUMMARY OF THE INVENTION

These needs are met by the invention, which uses: a resonant optical cavity, configured to perform in a cavity ring down spectroscopy (CRDS) mode and (partially) filled with a non-cavity-filling sample at a selected temperature and pressure; an intense collimated source of narrow band coherent light (preferably polarized) with a selectable wavelength; a light coupler to couple a light beam into and out of the cavity; and an absorption analyzer to receive the light coupled out of the cavity, to determine the absorption by the sample and the absorption due to cavity losses, and to provide a graphical or other representation of the sample absorption versus wavelength. The sample may have the form of a gas, a liquid, a thin film, a solid that is not in the form of a thin film (referred to herein as a "bulk solid") and any other form that does not completely fill the cavity.

In a preferred embodiment, two or more highly reflective, spaced apart mirrors are arranged to form an optically stable cavity. The sample, and any necessary sample support, has at least two substantially parallel interfaces with another selected medium (preferably, but not necessarily, a vacuum) within the cavity and is arranged so that each of these parallel interfaces intercepts the propagating light beam at an incidence angle equal to the Brewster angle for that interface and for the wavelength used. This arrangement ensures that substantially all of a p-wave polarization component (parallel to a plane of incidence) of the light beam is transmitted into and out of the sample, with little or no light beam reflection at either sample/medium interface. The light beam is introduced into the optical cavity, makes two or more round trips through the optical cavity and through the sample, is extracted from the cavity, and is analyzed to estimate the absorption losses within the sample. This analysis is performed at one or more selected wavelengths, and the resulting absorption spectrum is used to determine one or more characteristics of the sample, such as presence of, or concentration of, a target molecule within the sample.

DESCRIPTION OF BEST MODES OF THE INVENTION

The invention relies on an alternative approach to evanescent wave CRDS for quantitative measurements in non-cavity-filling samples. In one embodiment, an interface of the sample (including a sample support interface, if a sample support is required) is positioned at Brewster's angle relative to the local propagation direction of the light beam inside the RDC. In a second embodiment, a specific coupled cavity structure within the RDC is created that is mechanically stable and does not interfere with the single exponential decay characteristic of the ring-down signal. A third embodiment is a monolithic cavity incorporating the first or second embodiment but allowing continuous flow of a gaseous or liquid sample across a portion of the light beam path.

Figure 1:
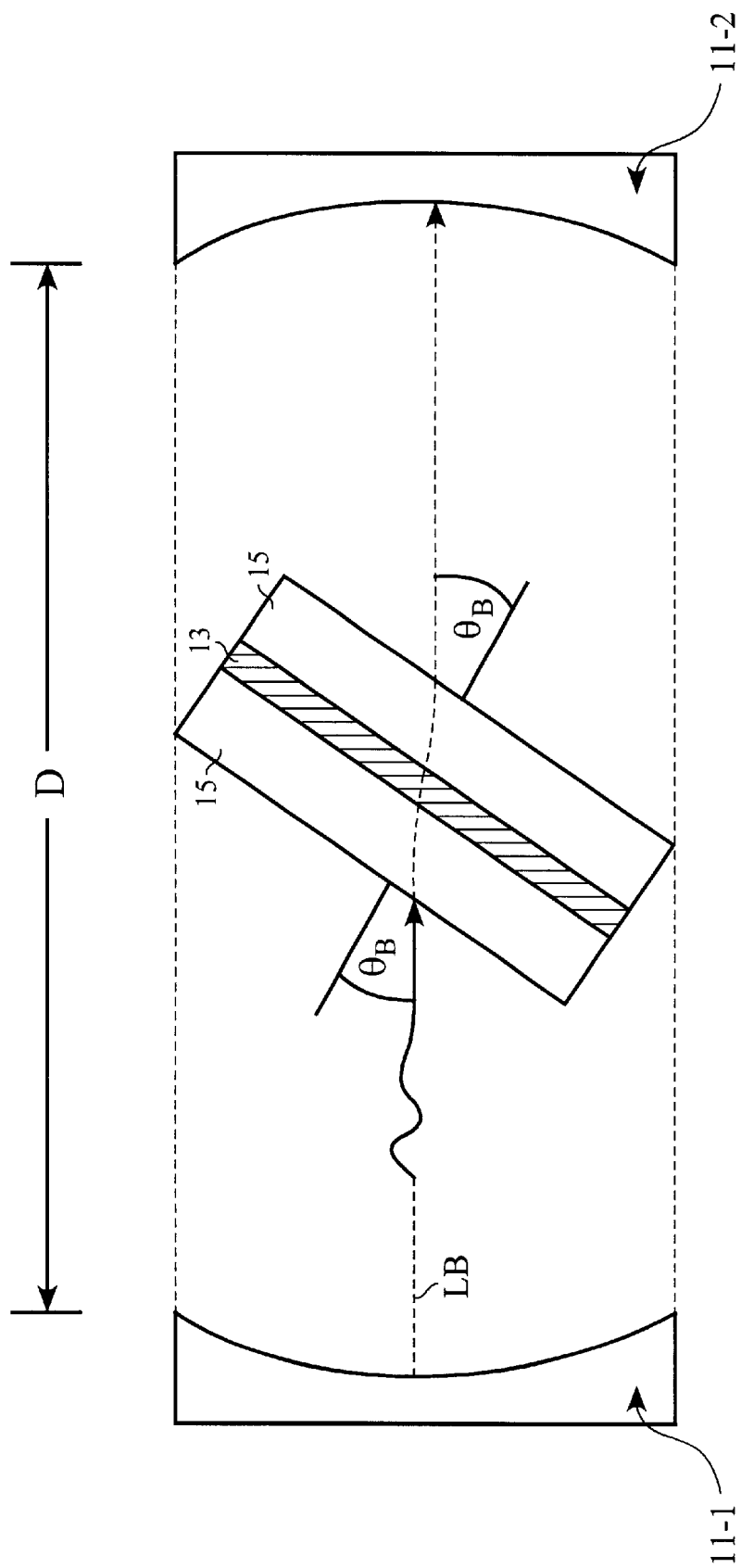
FIGS. 1, 3–5, 7 and 8A/8B are perspective views of suitable arrangement of a sample and sample support, relative to a longitudinal axis followed by a light beam according to the invention.
Figure 2:
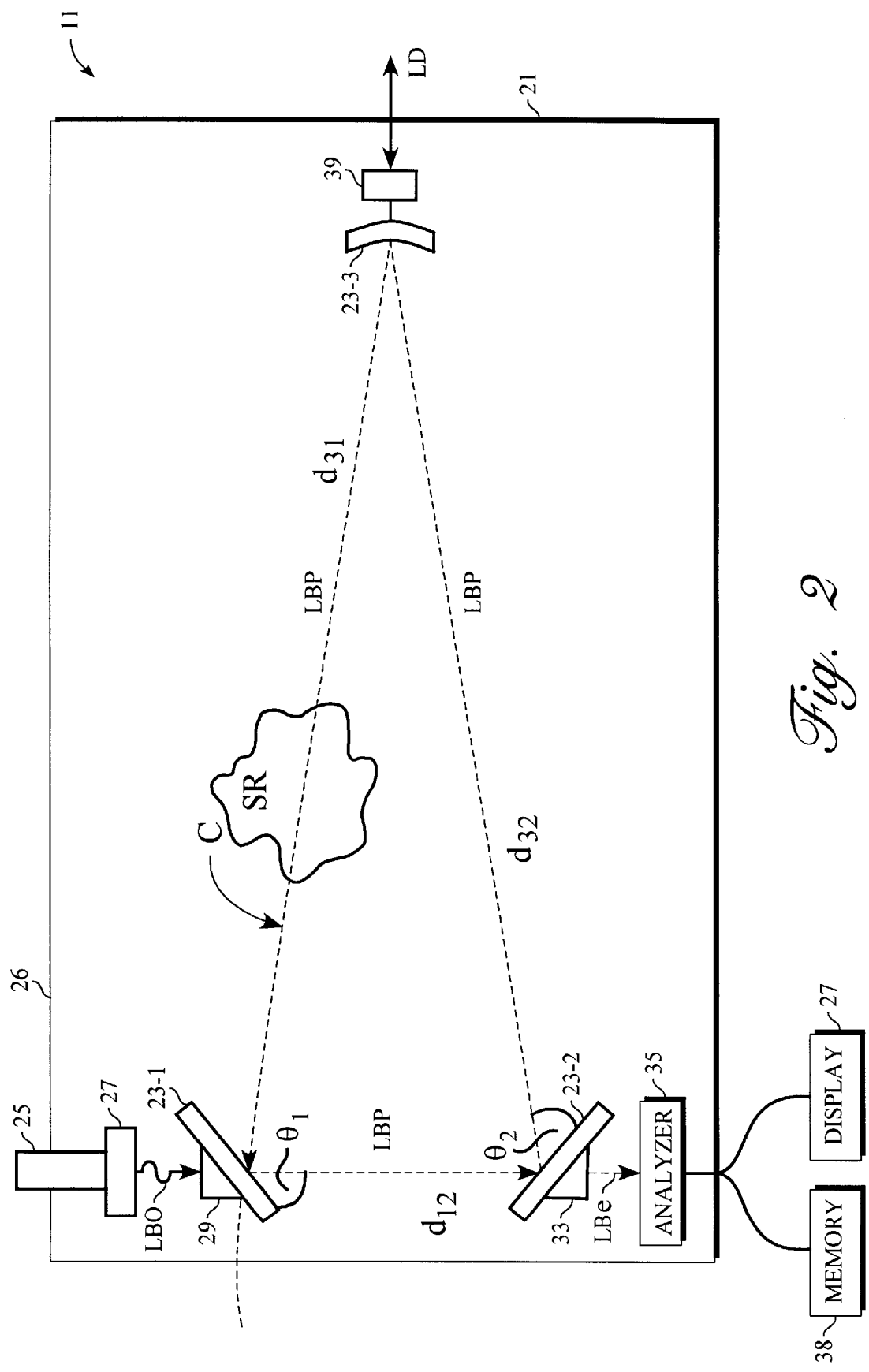
FIG. 2 is a schematic view of apparatus suitable for practicing the invention.

Consider an optical resonator that is formed by two highly reflecting mirrors, 11-1 and 11-2, as shown in FIG. 1. Alternatively, the resonator may have a ring configuration and include two or more highly reflecting mirrors, such as 23-1, 23-2 and 23-3, as shown in FIG. 2. For a given mirror separation, $d_{12}$, mirror curvatures, r1 and r2, and mirror reflectivities, R1 and R2, certain resonator geometries will be optically stable, allowing a properly directed light beam to execute numerous round trips within the cavity defined by the mirrors. For such an optically stable configuration, certain light beam wavelengths $\lambda$, determined with reference to the round trip distance $2 \cdot d_{12}$ and to the refractive index $n_{ref}$ of a medium located between the mirrors, 31-3 and 31-2, will support development of an optical resonator mode, longitudinal or transverse. A longitudinal mode wavelength $\lambda$ is determined by a phase round trip condition, such as $$\Delta\phi = 2\pi d_{12} n_{ref}/\lambda = 2\pi \cdot N (N=1,2,3,\ldots). \tag{3}$$

A transverse mode wavelength $\lambda$ is determined with reference to the effects of mirror geometry and mirror size on light beam diffraction within the optical cavity. Resonator stability conditions and resonator mode wavelengths are discussed in A. Yariv, *Optical Electronics,* Holt, Rinehart and Winston, New York, Third Edition, 1986, pp. 17–22, 87–120. For a two-mirror arrangement, such as that shown in FIG. 1, a transverse electromagnetic resonator mode, labeled $TEM_{m,n}$, can be approximated by Hermite-Gaussian polynomial functions $$H_{m,n}(x,y,z) = \{\omega 0/\omega(z)\} \cdot H_m(\sqrt{2}x/\omega((z)) \cdot H_n(\sqrt{2}y/\omega(z)), \tag{4}$$

$$\omega(z)/\omega 0 = \{1+(z/z0)^2\}^{-\frac{1}{2}}, \tag{5}$$

$$z0 = \pi \cdot \omega 0^2 \cdot n_{ref}/\lambda, \tag{6}$$

as discussed in Yariv, op cit, pp. 35–37. Here $\omega 0$ is a selected positive constant having the units of length and determined with reference to the mirror separation, $d_{12}$, and to the mirror radii, r1 and r2, and $H_p(w)$ is an Hermite polynomial, discussed in E. Merzbacher, *Quantum Mechanics,* John Wiley & Sons, New York, 1961, pp. 51–59.

The ring-down decay constant $\tau$ for the optical system is determined by the total RDC losses. For a background or reference measurement performed on an empty cavity, the total losses involve only mirror losses (non-perfect reflectivity, diffraction, etc.). For a cavity containing a non-cavity-filling sample, which may be mounted on or confined by a sample support, additional losses within the cavity include scattering, reflection and/or absorption at the support interfaces (undesirable) and absorption by the sample. The sample support may be a substrate, a closed container for the sample, a container having one, two or more apertures to allow fluid flow into and out of the container, or other suitable apparati that provide at least two substantially parallel interfaces for the sample material. The losses produced by the support can be measured by a wavelength scan within the cavity, sans sample. The sample absorption spectrum is then measured by "subtracting" the mirror losses and the support losses from the measured total losses.

In order to preserve the sensitivity of the CRDS technique, losses caused by the sample support within the cavity should be minimized. For any interface between first and second, different, substantially homogeneous materials and a selected wavelength $\lambda$, an incidence angle can be determined for which a monochromatic light beam with wavelength $\lambda$, incident upon the interface at that angle and having a light polarization direction that is parallel to a plane containing the interface, will be transmitted with no reflected component. This incidence angle, $\theta_B$, the Brewster angle for this interface, minimizes or eliminates optical intensity losses due to reflections at the interface. The Brewster angle is determined by the relationship $$\tan \theta_B = n_{ref,2}(\lambda)/n_{ref,1}(\lambda), \tag{7}$$

where $n_{ref,1}(\lambda)$ and $n_{ref,2}(\lambda)$ are the (real) refractive indices for the first and second media, respectively. See M. Born and E. Woff, *Principles of Optics,* Pergamon Press, Oxford, Fifth Edition, 1975, pp. 36–44, for a discussion of this relationship. The Brewster angles for water ($n_{ref,2}=1.33$) and for a typical glass ($n_{ref,2}=1.52$), relative to an interface with a vacuum, have the respective values of 53.061° and 56.310°.

The fractional intensity loss in the transmitted component of a p-polarized light beam incident on the interface at an angle $\theta 1=\theta_B+\delta\theta 1$ is approximately proportional to $\sin^2(\delta\theta 1)$ so that the intra-cavity optical loss in the transmitted component intensity will increase quite rapidly for small, non-zero values of $\delta\theta 1$; this increase in the reflected component intensity, from an ideal value of 0, will reduce CRDS sensitivity and should be minimized, preferably by arranging that the light beam incidence angle be as close as possible to the brewster angle $\theta_B$.

If a sample support is present, the sample support material is preferably chosen so that, for light beam wavelengths close to a selected central wavelength $\lambda$, the refractive index for the sample support is substantially equal to the refractive index of the sample. This choice reduces the reflective losses at a sample/support interface to approximately zero. This equality of refractive indices may be achieved only approximately, if a substantial bandwidth of wavelengths $\lambda$ is used for sample probing.

Apart from a natural desire to provide a system with relatively low optical losses, the low reflective losses associated with this embodiment have another, more quantitative advantage. Assume that the fractional optical loss and fractional absorption loss per round trip of the light beam are f1 and f2, respectively. Each of the fractions f1 and f2 will vary with wavelength and will have small uncertainties, $\delta$f1 and $\delta$f2, respectively, that are approximately proportional to f1 and f2: $\delta f1/f1 \approx \delta f2/f2$. If, say, the fractional optical loss f1 per round trip is 5–20 times that of the absorption loss f2, the variation or uncertainty in optical loss, f1+$\delta$f1, can overwhelm the variation or uncertainty in absorption loss, f2+$\delta$f2, and thus can mask a small but meaningful variation of absorption loss with varying wavelength. Thus, the order of magnitude of resolution in absorption loss per round trip with varying wavelength is determined, in large part, by the relative magnitude of optical loss per round trip.

FIG. 1 illustrates a preferred orientation of a non-cavity-filling sample 13, optionally associated with a sample support 15, relative to a light beam LB that moves between a first mirror 11-1 and a second mirror 11-2. The mirrors 11-1 and 11-2 have the respective selected mirror radii r1 and r2, have the respective selected reflectivity coefficients R1 and R2, are spaced apart a selected separation distance D facing each other, and define an optical cavity C1. The two-mirror optical resonator defined by the mirrors 11-1 and 11-2 is optically stable only if the parameters r1, r2 and D satisfy the constraints $$0 \leq (1-D/2\cdot r1)(1-D/2\cdot r2) \leq 1, \qquad (8)$$

as shown by Yariv, op cit, pp. 18–22. An optically unstable resonator having two mirrors arranged as shown in FIG. 1 will allow a light beam of a selected size to grow without limit and to expand beyond the boundaries of the mirrors.

The light beam LB in FIG. 1 approaches the sample 13 with an incidence angle substantially equal to $\theta B$ for the light beam wavelength $\lambda$ of interest. A sample support 15 is optionally provided for the sample 13, depending upon the form in which the sample is provided. If the sample 13 is a bulk solid, capable of maintaining its own shape, the sample support 15 may be deleted. If the sample 13 is a thin film, the sample support 15 may be a one-sided or two-sided mechanism that supports and maintains the thin film as a planar surface oriented at an incidence angle $\theta B$ for the light beam LB. If the sample 13 is a liquid, the sample support 15 may be a container that holds the liquid sample (and, optionally, allows the sample to flow in a selected direction).

FIG. 2 illustrates one embodiment of a system 21 for practicing the invention to obtain a spectrum for the sample. Two or more spaced apart optical reflectors ("mirrors"), 23-1, 23-2, 23-3, are configured to form an optical cavity C so that a light beam that travels from a first selected spot or region on a first mirror to a second selected spot or region on a second mirror will be reflected from the second mirror and will ultimately return to the first region on the first mirror, be reflected from the first mirror, and again propagate toward and be reflected from the second region of the second mirror.

In the ring configuration shown in FIG. 2, the cavity C is formed by three mirrors, at least one (23-3) having a curvilinear surface rather than a planar surface; the other two mirrors, 23-1 and 23-2, may have planar or curvilinear surfaces. Each of the first, second and third mirrors 23-i (i=1, 2, 3) has a reflecting surface with a reflection coefficient $r_i(\theta i, \lambda)$ ($\leq 1$) that depends upon the light beam incidence angle $\theta i$ at the mirror i and upon the (narrow band) wavelength $\lambda$ of the light beam incident thereon, and possibly on other variables as well. Each of the first and second mirrors, 23-1 and 23-2, preferably has a reflection coefficient $r_j(\theta j, \lambda)$(j=1, 2) that is very close to, but not equal to, 1.0, in a preferred range such as $0.98 \leq r_j(\theta j,\lambda) \leq 0.999$. A small fraction of the light beam incident upon mirror no. i will be transmitted through, rather than being reflected from, this mirror. In the embodiment illustrated in FIG. 2, the third mirror 23-3 preferably has a reflection coefficient $r_3(\theta 3,\lambda)$ that is as close to 1.0 as possible. The number of mirrors employed here may be two, three (as in FIG. 2), four or more.

A source 25 of coherent light, such as a visible or infrared laser with a selected narrow range of emission wavelengths, provides an initial light beam LB0 that is received by and passed through the first mirror 23-1 and thereafter propagates within the optical cavity along a chosen light beam path LBP. The incidence angle at which the initial light beam LB0 approaches the first mirror 23-1 from the backside is preferably chosen to be approximately equal to the incidence angle $\theta 1$ for the light beam path LBP at the first mirror 23-1. The light beam source 25 has an associated light beam wavelength discrimination device 16 that provides a light beam with a selectable wavelength $\lambda$ having a line width that $\Delta n'$ that is preferably in the range $0.001 \text{ cm}^{-1} \leq \Delta n' \leq 1 \text{ cm}^{-1}$, or smaller if desired. Alternatively, the optical cavity C may have another optical coupling means, such as an acoustic-optical or electro-optical modulator, to couple the light beam LB0 into the cavity.

The initial light beam LB0 is passed through a beam polarizer 27 (optional) and through a first cavity coupler 29 that couples the initial light beam into the optical cavity C. The cavity coupler 29 may be merely a selected portion of the back side of the first mirror 23-1 that is specially configured and/or treated to allow a substantial, and measurable, portion ($\approx$0.1–2 percent) of the initial light beam LB0 to pass through the first mirror and into the cavity C, or the cavity coupler may be more elaborate. After the light beam enters the cavity C, the light beam follows the light beam path LBP from one mirror to the next, possibly losing a small amount of its light beam intensity I at each reflection from each mirror 23-i.

The three mirrors, 23-1, 23-2 and 23-3, and the optical cavity C formed by the mirrors, are located within a container 31 whose interior pressure can be controlled, if desired. The sample S may be a gas, a liquid or an optically thin solid, and is located in a sample region SR of the interior of the container 31 that is intersected by the light beam path LBP, preferably as indicated in FIG. 1. Each time the light beam passes through the sample region SR, a small fraction of the light beam intensity is absorbed by the molecule(s) contained in the sample S. The sample region SR includes less than all of the optical cavity.

At a selected one of the mirrors (shown as the second mirror 23-2 in FIG. 1 for definiteness), a selected, measurable small fraction of the light beam is extracted from the optical cavity C by a second cavity coupler 33. Preferably, this second small fraction is in the range 0.1–2 percent, but may be smaller or larger if desired. The extracted light defines an extracted light beam LBe that is received by a light beam analyzer 35. The analyzer 35 analyzes the light beam LBe and determines the amount of sample absorption and cavity loss, referred to collectively as the total light beam attenuation A, that the light beam intensity has experienced in its peregrinations within the cavity C. The total attenuation A includes a portion due to optical losses $A_{cav}$ arising from beam reflections at each mirror and a residual portion $A_{res}$ due to absorption of the light beam intensity by the sample S. After the attenuation $A=A_{cav} \cdot A_{res}$ has been determined by the analyzer 35 for one or more wavelengths $\lambda$, the numerical value for the attenuation is visually displayed by a visual display module 37 and/or stored in a memory module 39 for subsequent use.

Assume, initially, that the optical cavity operates in a single mode. The (very small) fraction of light beam intensity, for a given wavelength and a given sample concentration, absorbed by the sample S is assumed to approximately obey a Beers-Lambert exponential decay law so that $$A(x)/A(0)=1-\exp(-\alpha x), \qquad (9)$$

where x is the total distance propagated through the sample by the light beam, $\alpha=\alpha(\lambda,\rho)$ is a characteristic absorption coefficient for the sample and $\rho$ is a measure of sample concentration in the sample region SR of the cavity. For very low sample concentrations $\rho$, the absorption coefficient $\alpha(\lambda,\rho)$ will be approximately proportional to $\rho$.

Let $d_{12}$, $d_{23}$ and $d_{31}$ be the known distances from the first mirror 23-1 to the second mirror 23-2, from the second mirror 23-2 to the third mirror 23-3, and from the third mirror 23-3 to the first mirror 23-1, respectively, with $$d=d_{12}+d_{23}+d_{13}. \qquad (10)$$

The fractional attenuation $\Delta$Att in light beam intensity experienced in one round trip within the cavity C is $$\Delta Att=1-\exp(-\beta_{opt,1}-\beta_{opt,2}-\beta_{opt,3}-\alpha \cdot d),tm \qquad (11)$$

$$\beta_{opt,i}=ln(1/\gamma_{opt,i})(i=1, 2, 3), \qquad (12)$$

where $\gamma_{opt,i}=\gamma_{opt,i}(\theta i,\lambda)$ (i=1, 2, 3) is the fractional loss in light beam intensity of wavelength $\lambda$ experienced by reflection of the light beam LB once at an incidence angle $\theta i$ at mirror no. i. The formalism adopted in Eq. (11) incorporates the assumption that the sample region SR includes all of the light beam path LBP. Where, as here, the sample region SR includes only a fraction f of the light beam path, the quantity $\alpha \cdot d$ in Eq. (11) is replaced by the quantity $f \cdot \alpha \cdot d$.

Where a light beam enters the cavity with initial intensity I(0) at mirror no. 1, propagates n times around the cavity circuit and exits from the cavity at mirror no. 2, the ratio of the remaining light beam intensity I(n) of the exiting beam after n cycles or round trips to the initial light beam intensity is given by $$I(n)/I(0)=\exp\{-n \cdot (\beta_{opt,1}+\beta_{opt,2}+\beta_{opt,3})-n \cdot \alpha \cdot d \}, \qquad (13)$$

if the optical cavity is resonant for the light beam wavelength $\lambda$. For a wavelength $\lambda$ for which the optical cavity is not resonant, the intensity ratio for a TEMO$_{0,0}$ light beam mode is approximately $$I(n)/I(0)=\exp\{-n \cdot (\beta_{opt,1}+\beta_{opt,2}+\beta_{opt,3})-n \cdot \alpha \cdot d+2\pi inn_s d/\lambda\}, \qquad (14)$$

where the quantity $2\pi inn_s d/\lambda\}$ in the exponent in Eq. (14) is to be computed modulo $2\pi$ and $n_s$ refers to the (measured) sample refractive index.

Where, for example, the light beam LB0 enters the optical cavity C at the first reflector 23-1 and exits from the optical cavity C at the second reflector 23-2, the light beam intensity ratio is approximately $$I(n)/I(0)=\exp\{-\chi 1-n \cdot (\beta_{opt,1}+\beta_{opt,2}+\beta_{opt,3})-\alpha \cdot (n \cdot d+d_{12})+2\pi i(n \cdot d+d_{12})n_s/\lambda-\chi 2\}, \qquad (15)$$

where $\chi 1=\chi 1(\theta 1)$ and $\chi 2=\chi 2(\theta 2)$ are the one-time attenuation factors associated with coupling the light beam into the optical cavity and out of the optical cavity, respectively. The known quantities are I(0), $\chi 1$, $\chi 2$, $\beta_{opt,1}$, $\beta_{opt,2}$, $\beta_{opt,3}$, n, $n_s$, d and $d_{12}$;. The absorption coefficient $\alpha$ may be unknown at this point and can be estimated using the extracted light beam intensity I($\lambda$;meas) measured at the beam analyzer 25 in FIGS. 1 and 2 and the relation $$\infty I(\lambda;meas)/I(0)=\Sigma I(n)/I(0)n=0=\exp\{-\chi 1-\chi 2-a \cdot d_{12}+2\pi i(d_{12}/1)\}/\{1-\exp\{-\beta_{opt,1}+\beta_{opt,2}+\beta_{opt,3})-\alpha \cdot d+2\pi i(d \cdot n_s/\lambda)\}, \qquad (16)$$

which should be true at each wavelength $\lambda$ for which intensity measurements are taken. If the quantity $\alpha \cdot d_{12}$ in the numerator in Eq. (16) can be ignored relative to the magnitudes of the other terms in the numerator, Eq. (16) simplifies to $$\alpha \cdot d=(\beta_{opt,1}+\beta_{opt,2}+\beta_{opt,3})-2\pi i(d \cdot n_s/l)-ln1-\{I(0)/I(\lambda;meas)\}\exp\{-\chi 1-\chi 2 \cdot 2\pi i(d_{12} \cdot n_s/\lambda)\}. \qquad (17)$$

Where the cavity is resonant for the wavelength $\lambda$, the quantities $2\pi i(d \cdot n_s/l)$ and $2\pi i(d_{12} \cdot n_s/\lambda)$ in Eqs. (16) and (17) may be ignored. Alternatively, some other method can be used to determine or estimate the value of the absorption coefficient $\alpha(\lambda;\rho)$, using Eq. (15) or another suitable relation.

For a selected wavelength $\lambda$, preferably the optical cavity C is provided with a distance control device that controllably varies the cavity round trip distance d so that the cavity is resonant for a longitudinal mode for the wavelength $\lambda$: $d=N \cdot \lambda$, where N is a positive integer. The distance control device may, for example, be a longitudinal displacement device connected to one of the cavity mirrors (23-3 in FIG. 2) that translates that mirror in a selected longitudinal direction, denoted LD, in order to controllably vary the cavity round trip distance d. The round trip distance d may be controlled by dithering the attached mirror 23-3 or by providing frequency locking, using techniques such as those discussed by Ahola, Hu and Ikonenm Rev. Sci Instrum., vol. 69 (1998) pp. 1934–1937, and by Shaddock, Gray and McClelland, Optics Lett., vol. 24 (1999) pp. 1499–1501.

Figure 3:
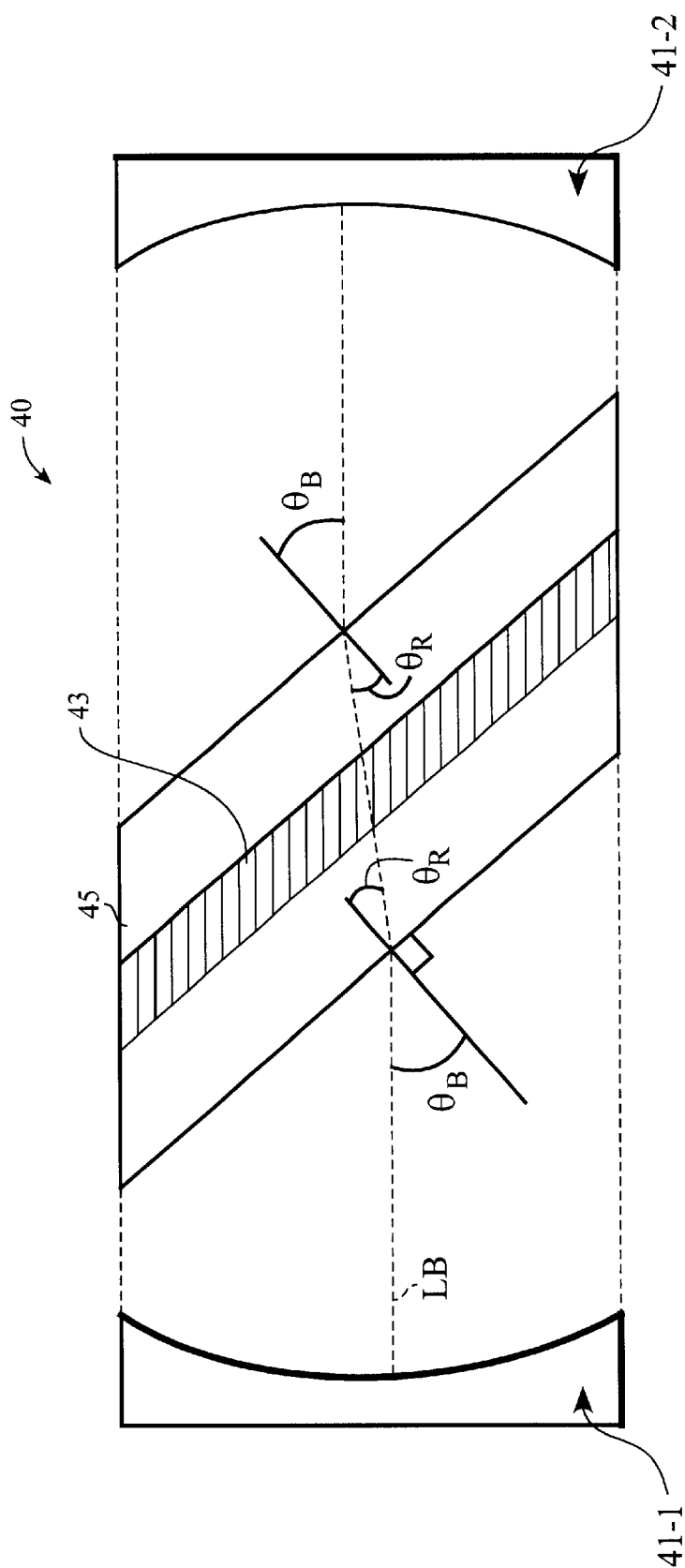

FIG. 3 shows another embodiment of presentation of the sample 43 to the light beam LB, in an optical cavity defined by two (or more) mirrors, 41-1 and 41-2. A support 45 for the sample 43 includes a surrounding bulk solid of material, selected to have a refractive index $n_{support}$ that is preferably approximately equal to the refractive index $n_s$ for the sample.

Figure 4:
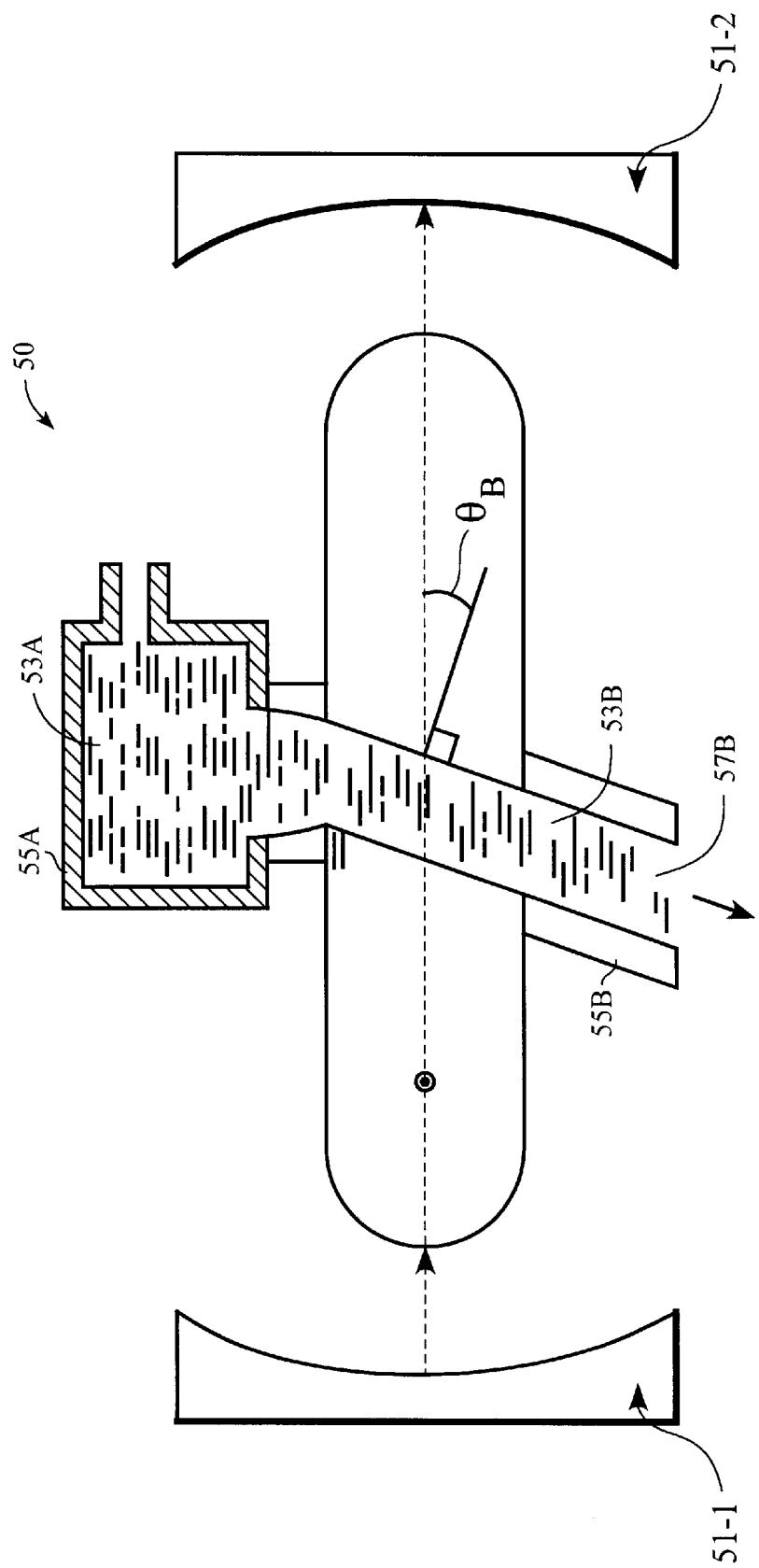

FIG. 4 shows another embodiment of presentation of the sample 53 to the light beam LB, in an optical cavity defined by two (or more) mirrors, 51-1 and 51-2. A first quantity of a sample 53A is held in a sample reservoir 55A that serves as part of a sample support. the sample reservoir 53A is connected to a channel 55B that contains a flowing second quantity of the sample 53B. The first quantity of liquid sample 53A is optionally replenished in the reservoir 55A using a reservoir inlet 57A. The second quantity of sample 53B optionally exits from the channel 55B at a channel outlet 57B. A portion of the channel 55B containing the flowing liquid sample 53B is positioned across an axis along which the light beam LB propagates, and this portion of the channel is surrounded by another container 59 that contains a liquid or solid material having a refractive index at a selected wavelength $\lambda$ that corresponds to, but is not necessarily identical to, the refractive index of the sample 53B. A mirror, 51-1 and 51-2, located at each end of the axis defines an optical cavity for the sample.

Figure 5:
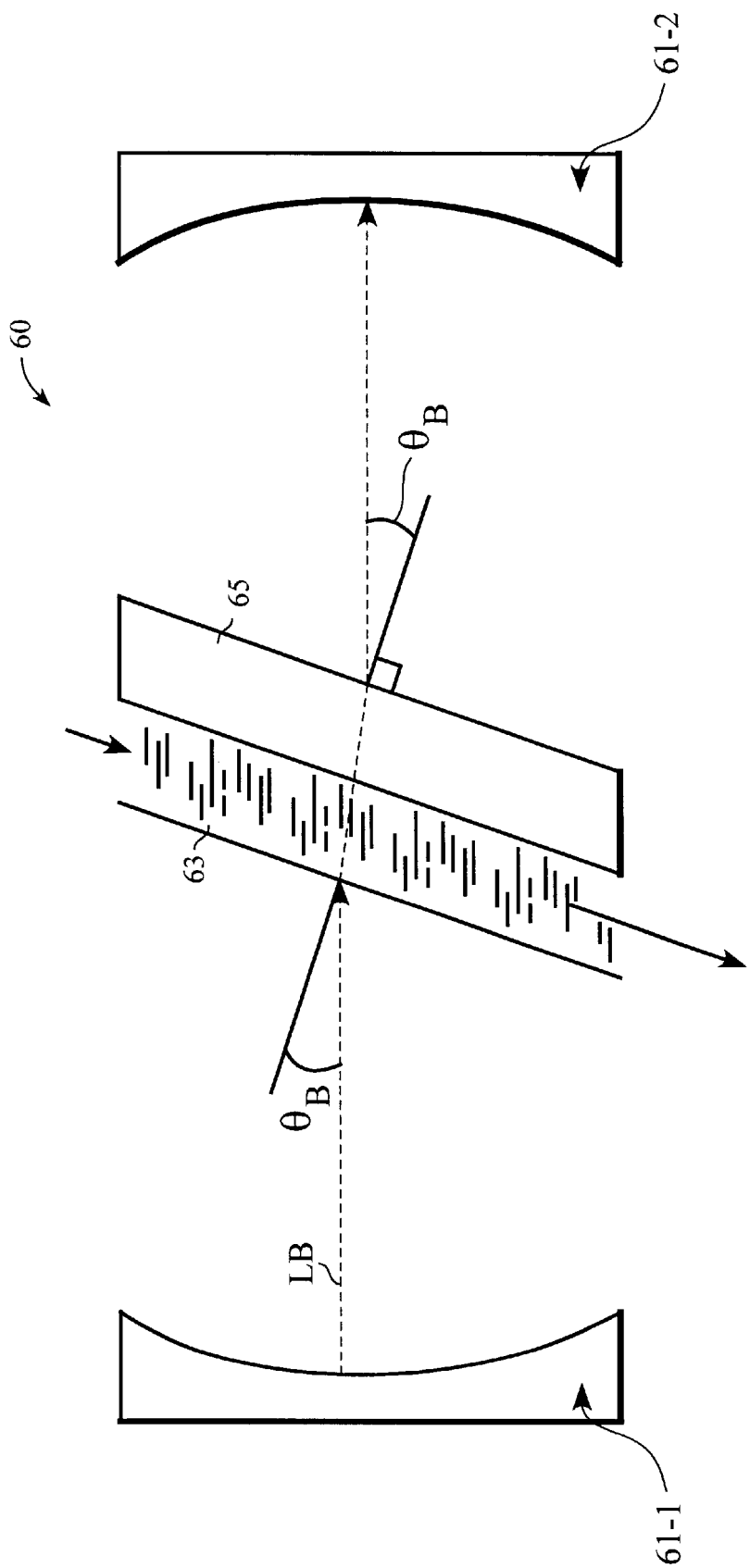

FIG. 5 shows another embodiment of presentation of the sample 63 to the light beam LB, in an optical cavity defined by two (or more) mirrors, 61-1 and 61-2. FIG. 5 is similar to FIG. 4, except that FIG. 5 provides only a sample support 65 for the flowing liquid 63 and does not include a separate container that is analogous to the container 59 in FIG. 4.

Figure 6:
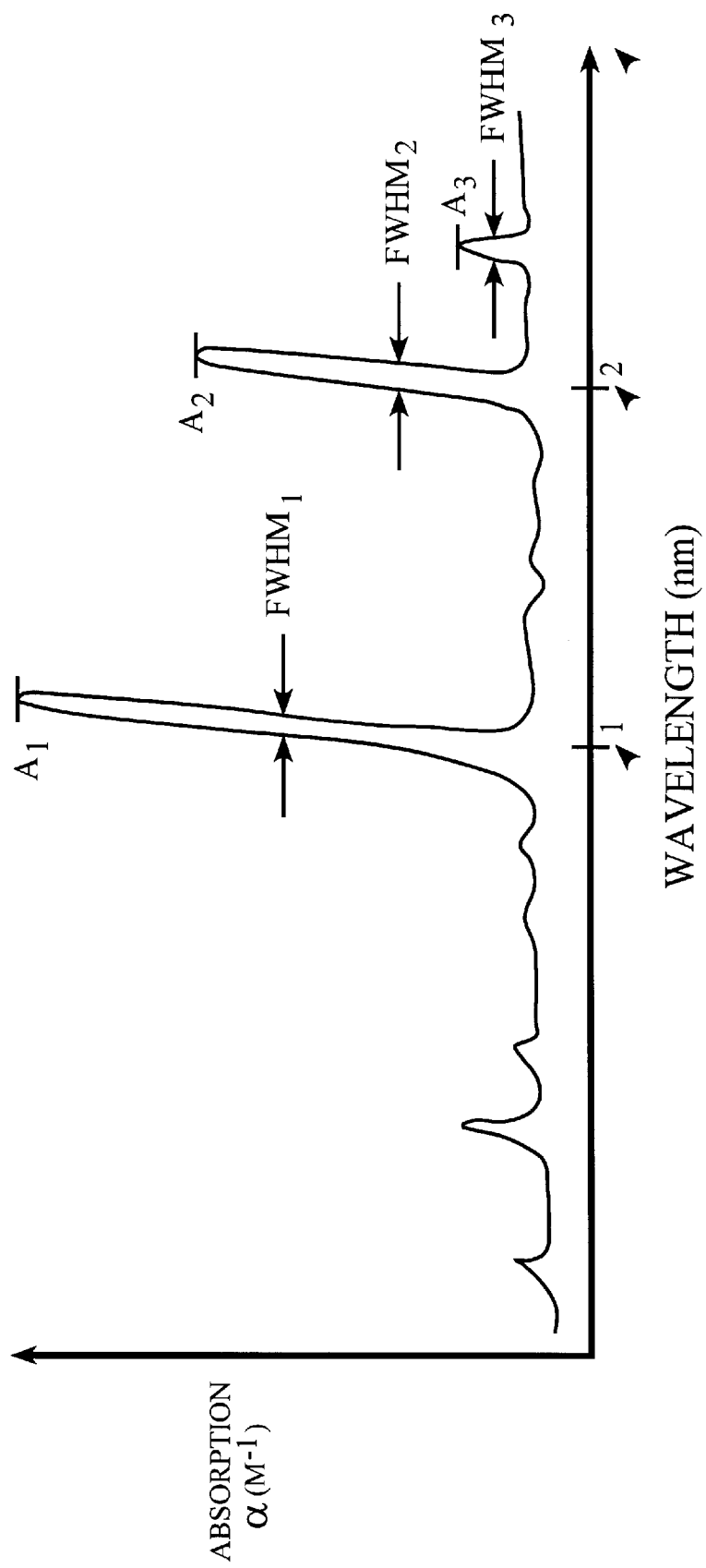
FIG. 6 is a graphical representation of an absorption spectrum for a sample.

FIG. 6 is a graphical representation of a typical absorption spectrum that might be obtained for sample, using the system shown in FIG. 2. Each of a sequence of prominent peaks at identifiable wavelengths, $\lambda=\lambda 1, \lambda 2, \lambda 3$, will have a characteristic absorption amplitude, $A=A1, A2, A3$, and each such peak will have a corresponding full width at half maximum (FWHM) that is preferably quite narrow, with a corresponding wave number width $\Delta v'$ that is preferably no greater than 0.001–1 cm$^{-1}$.

Figure 7:
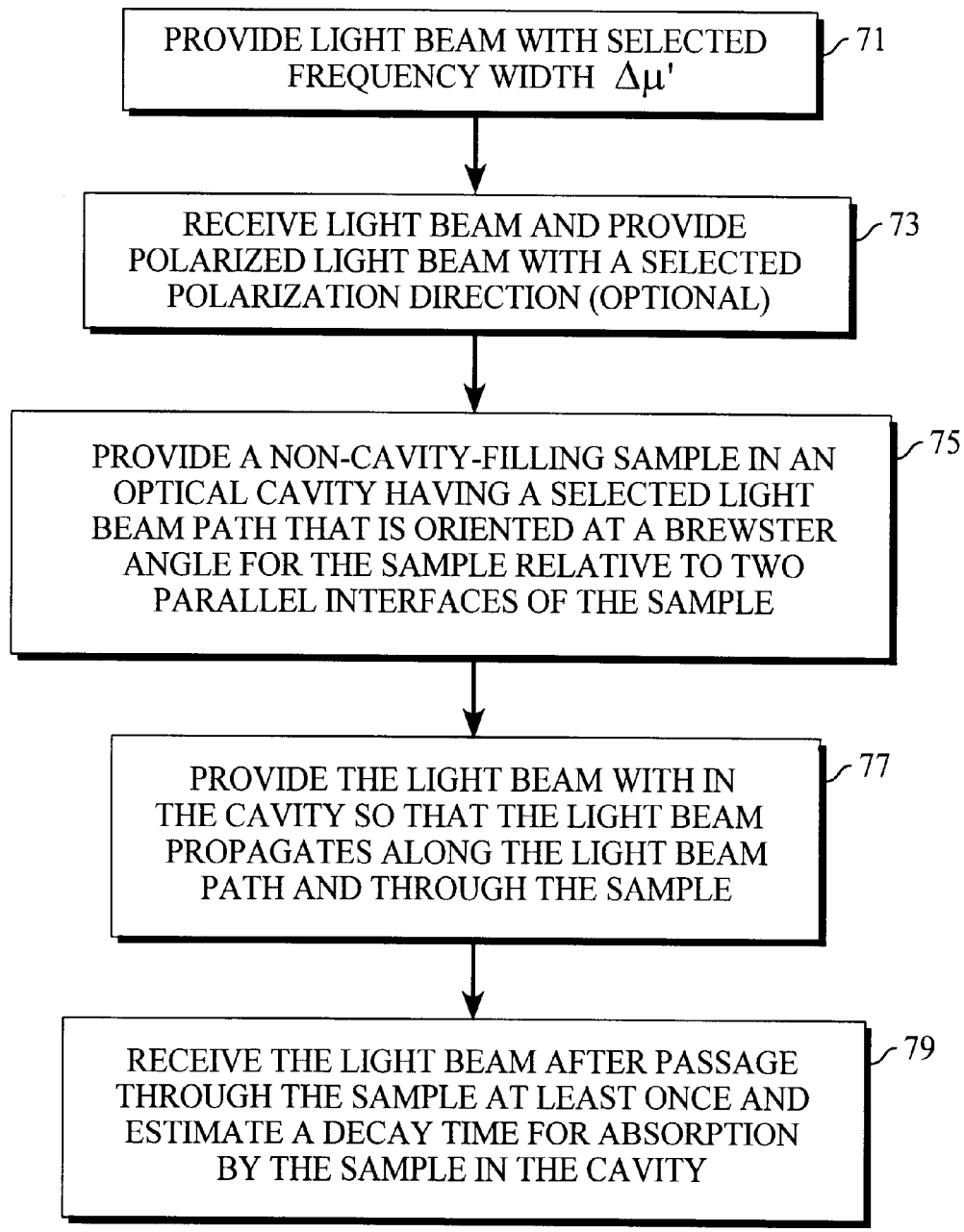
Figure 7:
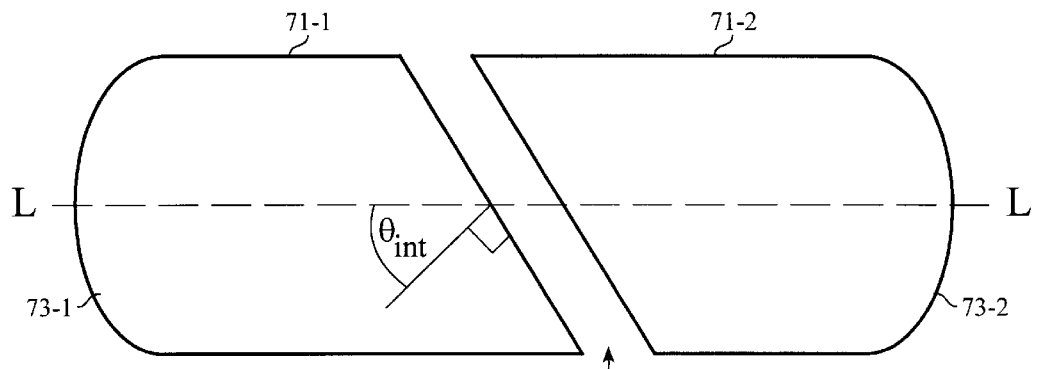

FIG. 7 illustrates another embodiment of the invention, wherein most of the optical cavity C is filled with an optically transparent solid, 71-1 and 71-2, and two polished and curvilinear ends, 73-1 and 73-2, of this solid serve as the mirrors defining the cavity. The two solid components, 71-1 and 71-2, form a cylinder, if pressed together. However, these two solid components, 71-1 and 71-2, are spaced apart and are each cut at the same interface angle, $\theta=\theta_{int}$, that is chosen to satisfy $$\tan\theta_{int}=n(\text{solid})/n(\text{sample}). \quad (18)$$

Here, n(solid) and n(sample) are the refractive indices of the solid components and of a sample that is positioned in the space 75 between the two solid components. The refractive indices n(solid) and n(sample) will each vary with wavelength, but it may be possible to choose these materials so that their ratio is approximately constant across a modest bandwidth of wavelengths.

Figure 8A:
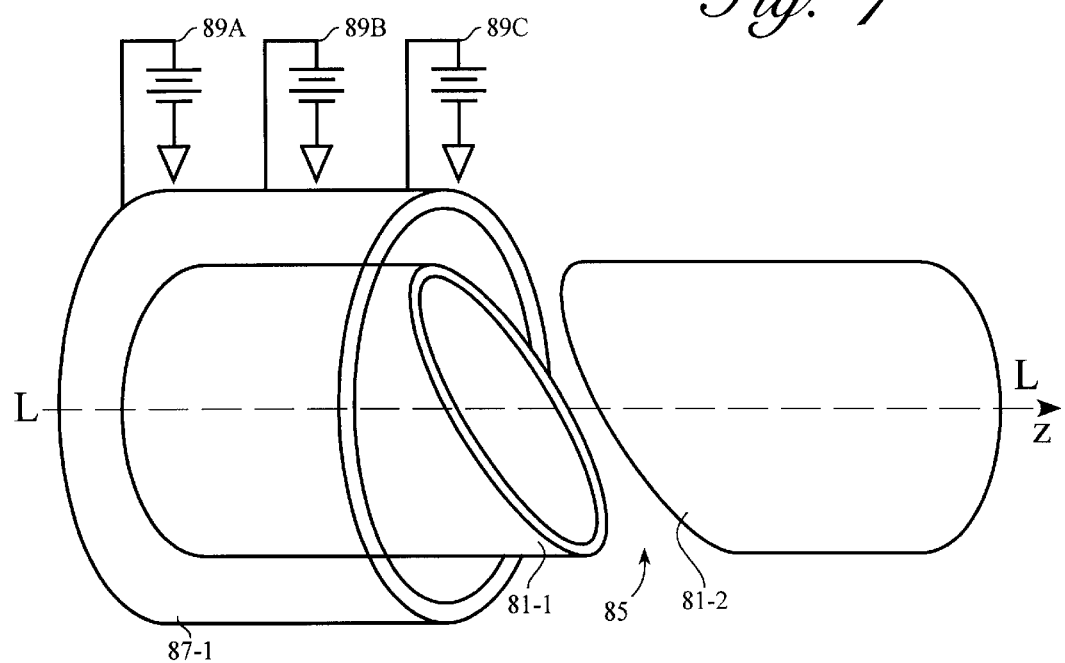
Figure 8B:
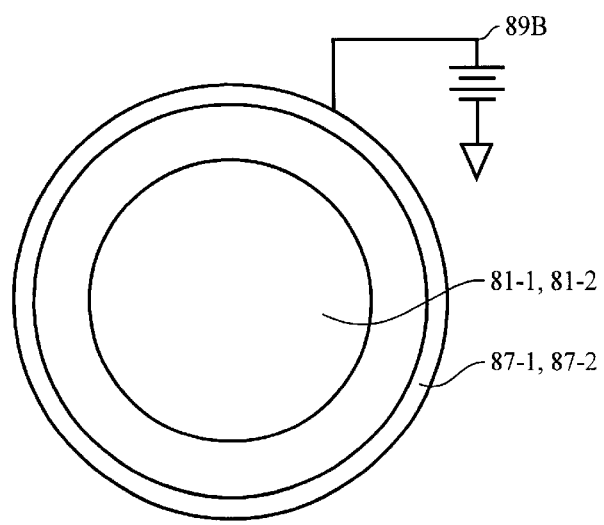

FIGS. 8A (side view) and 8B (end view) illustrates a variation on the embodiment shown in FIG. 7, where the material that forms the solid components, 81-1 and 81-2, is dielectrically active: the refractive index n(solid) depends upon the local strength of an electrical field E(z) that is imposed on the solid. One or both solid components, 81-1 and 81-2, is circumferentially surrounded by an electrically conducting plate, 87-1 and 87-2, having an electrical field E(z) that can be varied along a longitudinal axis LL: the refractive index n(solid) can be made to vary with a longitudinal coordinate z, if desired. The electrical field E(z) is provided by a sequence of power supplies, 89A, 89B and 89C, that are connected to the plates, 87-1 and 87-2, at various locations. The plates, 87-1 and 87-2, may be segmented to allow each plate segment to carry a different electrical field $\underline{E}(z)$.

In another version, the imposed electrical field E is varied with the light beam wavelength $\lambda$ so that the refractive index ratio appearing on the left hand side of Eq. (18) is substantially constant with varying $\lambda$. Suitable solid materials that are dielectrically active include $LiNbO_3$, $LiTaO_3$ and KDP.

A solid sample, preferably in the form of a thin film, that is positioned in the cavity may be teflon, kapton, polystyrene or other materials. A fluid sample that is positioned in the cavity may be water, methyl alcohol, ethyl alcohol, methylene, ethylene or similar non-organic or organic materials.

What is claimed is:

1. Apparatus for measuring light absorption in a non-cavity-filling sample having a refractive index, the apparatus comprising:

a source of a light beam having a selected beam wavelength width and including at least one selected wavelength $\lambda$;

a ring down optical cavity, including at least first and second spaced apart light beam reflectors, to receive and reflect the light beam and to establish a resonant mode for light having the selected wavelength $\lambda$;

a non-cavity-filling sample, positioned in the optical cavity, having a known refractive index and having at least two substantially parallel interfaces that are oriented to receive and transmit the light beam at an incidence angle substantially equal to Brewster's angle for the sample; and a measurement mechanism for receiving the light beam after the beam has been reflected at least once from each reflector and for estimating a decay time for the light beam that includes absorption of the light beam by the sample.

2. The apparatus of claim 1, wherein said sample is a fluid, further comprising a sample support that supports said sample, that has at least two substantially parallel interfaces that are oriented to receive and transmit said light beam at an incidence angle substantially equal to Brewster's angle for said sample, and that has a support refractive index that is substantially equal to said sample refractive index.

3. The apparatus of claim 2, wherein said sample support comprises a material that attenuates an intensity of said light beam at said selected wavelength at no more than 100 ppm for one passage of said light beam through said sample support.

4. The apparatus of claim 2, wherein said fluid sample is substantially contiguous to and flows over at least a portion of each of said two parallel interfaces of said sample support.

5. The apparatus of claim 2, wherein said fluid sample is drawn from a group of liquids consisting of water, methyl alcohol, ethyl alcohol, methylene and ethylene.

6. The apparatus of claim 2, wherein said sample support is a solid material that fills said cavity, except for a region of said cavity that is occupied by said sample.

7. The apparatus of claim 6, wherein said sample support material is a dielectrically active material whose refractive index varies with strength of an electrical field applied to said sample support material.

8. The apparatus of claim 7, wherein electrical fields having at least two different strength values are applied to said sample support material.

9. The apparatus of claim 7, wherein said sample support material has said electrical field applied thereto and said electrical field strength is chosen according to a ratio of said sample refractive index to said sample support refractive index at a selected wavelength.

10. The apparatus of claim 1, wherein said sample is a solid material drawn from a group of solids consisting of a thin film and a bulk solid.

11. The apparatus of claim 10, wherein said sample is a thin film selected from a group of thin film materials consisting of polystyrene, Teflon and Kapton.

12. The apparatus of claim 10, wherein said sample is a thin film, further comprising a sample support that supports said sample, that has at least two substantially parallel interfaces that are oriented to receive and transmit said light beam at an incidence angle substantially equal to Brewster's angle for said sample, and that has a support refractive index that is substantially equal to said sample refractive index.

13. The apparatus of claim 12, wherein said sample support comprises a material that attenuates an intensity of said light beam at said selected wavelength at no more than 100 ppm for one passage of said light beam through said sample support.

14. The apparatus of claim 1, wherein said selected wavelength lies in a wavelength range $0.3 \times 10^{-2}$ $\mu m \leq \lambda \leq 300$ $\mu m$.

15. The apparatus of claim 1, wherein said selected beam wavelength width lies in a range $0.001$ cm$^{-1} \leq \Delta v' \leq 1$ cm$^{-1}$.

16. The apparatus of claim 1, further comprising a light beam polarization mechanism for receiving said light beam from said source and for producing a modified light beam with a selected polarization direction.

17. The apparatus of claim 16, wherein said selected polarization direction is substantially parallel to said at least two parallel interfaces of said sample.

18. The apparatus of claim 16, wherein said selected polarization direction is substantially perpendicular to said at least two parallel interfaces of said sample.

19. The apparatus of claim 16, wherein said measurement mechanism comprises a light beam intensity measurement mechanism for receiving and measuring the intensity of said light beam with a polarization direction determined with reference to said selected polarization direction, and for comparing the measured light beam intensity with a reference intensity that is associated with said light beam before said light beam has been reflected from said at least two reflectors.

20. A method for measuring light absorption in a non-cavity-filling sample having a refractive index, the method comprising:

providing a light beam having a selected beam wavelength width that includes at least one selected wavelength $\lambda$;

receiving the light beam in a ring down optical cavity, including at least first and second spaced apart light beam reflectors, that provides a resonant mode for light having the selected wavelength $\lambda$, and reflecting the light beam from each of the reflectors at least once;

positioning a non-cavity-filling sample in the optical cavity, the sample having a known refractive index and having at least two substantially parallel interfaces that are oriented to receive and transmit the light beam at an incidence angle substantially equal to Brewster's angle for the sample; and receiving the light beam, after the beam has been reflected at least once from each reflector, and estimating a decay time for the light beam that includes absorption of the light beam by the sample.

21. The method of claim 20, further comprising:

choosing said sample to be a fluid; and providing a sample support that supports said sample, that has at least two substantially parallel interfaces that are oriented to receive and transmit said light beam at an incidence angle substantially equal to Brewster's angle for said sample, and that has a support refractive index that is substantially equal to said sample refractive index.

22. The method of claim 21, further comprising choosing said sample support to include a material that attenuates an intensity of said light beam at said selected wavelength at no more than 100 ppm for one passage of said light beam through said sample support.

23. The method of claim 21, further comprising positioning said fluid sample to be substantially contiguous to and to flow over at least a portion of each of said two parallel interfaces of said sample support.

24. The method of claim 21, further comprising drawing said liquid sample from a group of liquids consisting of water, methyl alcohol, ethyl alcohol, methylene and ethylene.

25. The method of claim 20, further comprising choosing said sample support to be a solid material that substantially fills said cavity, except for a region of said cavity occupied by said sample.

26. The method of claim 20, further comprising choosing said sample support material to be a dielectrically active material whose refractive index varies with strength of an electrical field applied to said sample support material.

27. The method of claim 26, further comprising applying said electrical fields having at least two different strength values to said sample support material.

28. The method of claim 26, further comprising applying said electrical field to said sample support and choosing said electrical field strength according to a ratio of said sample refractive index to said sample support refractive index at a selected wavelength.

29. The method of claim 20, further comprising choosing said sample to be a solid material drawn from a group of solids consisting of a thin film and a bulk solid.

30. The method of claim 29, further comprising choosing said sample to be a thin film selected from a group of thin film materials consisting of polystyrene, Teflon and Kapton.

31. The method of claim 29, further comprising:

choosing said sample to be a thin film; and providing a sample support that supports said sample, that has at least two substantially parallel interfaces that are oriented to receive and transmit said light beam at an incidence angle substantially equal to Brewster's angle for said sample, and that has a support refractive index that is substantially equal to said sample refractive index.

32. The method of claim 31, further comprising choosing said sample support to include a material that attenuates an intensity of said light beam at said selected wavelength at no more than 100 ppm for one passage of said light beam through said sample support.

33. The method of claim 20, further comprising choosing said selected wavelength to lie in a wavelength range $0.3 \times 10^{-2} \, \mu\text{m} \leq \lambda \leq 300 \, \mu\text{m}$.

34. The method of claim 20, further comprising choosing said selected beam wavelength width to lie in a range $0.001 \, \text{cm}^{-1} \leq \Delta v' \leq 1 \, \text{cm}^{-1}$.

35. The method of claim 20, further comprising receiving said light beam from said source and for producing a modified light beam with a selected polarization direction.

36. The method of claim 35, further comprising choosing said selected polarization direction to be substantially parallel to said at least two parallel interfaces of said sample.

37. The method of claim 35, further comprising choosing said selected polarization direction to be substantially perpendicular to said at least two parallel interfaces of said sample.

38. The method of claim 35, further comprising:

receiving and measuring the intensity of said light beam with a polarization direction determined with reference to said selected polarization direction; and comparing the measured light beam intensity with a reference intensity that is associated with said light beam before said light beam has been reflected from said at least two reflectors.

* * * * *